(12) United States Patent  (10) Patent No.: US 8,377,007 B2
Moosheimer et al.  (45) Date of Patent: Feb. 19, 2013

(54) LABEL FOR PLACING ON A SYRINGE BODY, AND SYRINGE BODY

(75) Inventors: Ulrich Moosheimer, Hohenkammer (DE); Timo Hoelzl, Pfaffenhofen (DE)

(73) Assignee: Schreiner Group GmbH & Co. KG, Oberschleissheim (DE)

( * ) Notice: Subject to any disclaimer, the term of this patent is extended or adjusted under 35 U.S.C. 154(b) by 169 days.

(21) Appl. No.: 12/806,660

(22) Filed: Aug. 18, 2010

(65) Prior Publication Data

US 2011/0066113 A1 Mar. 17, 2011

(30) Foreign Application Priority Data

Sep. 1, 2009 (DE) .......................... 10 2009 039 572

(51) Int. Cl.
*A61M 5/32* (2006.01)
(52) U.S. Cl. ....................................... 604/192
(58) Field of Classification Search .................. 604/110, 604/189, 192, 197, 263; 206/365
See application file for complete search history.

(56) References Cited

U.S. PATENT DOCUMENTS

| 3,658,061 A | 4/1972 | Hall |
| 2002/0065488 A1 | 5/2002 | Suzuki et al. |
| 2007/0260191 A1 | 11/2007 | Prais et al. |
| 2009/0054847 A1 * | 2/2009 | Bauss et al. .................. 604/192 |

FOREIGN PATENT DOCUMENTS

| DE | 20 2008 017 330 | | 7/2009 |
| DE | 202008017330 U1 * | | 7/2009 |
| WO | WO 2006/105807 | | 10/2006 |
| WO | WO 2006105807 A1 * | | 10/2006 |

* cited by examiner

*Primary Examiner* — Theodore Stigell
(74) *Attorney, Agent, or Firm* — Collard & Roe, P.C.

(57) ABSTRACT

A label for placing on a syringe body has a first foil portion, which can be wound around a syringe body, a needle-receiving means for protecting against injuries by the syringe needle, having at least one second foil portion and a shaped plastic part that can be pressed on laterally against the syringe needle, and a transition area via which the needle-receiving means is connected pivotably to the first foil portion. The transition area protrudes laterally over the first foil portion in a first direction, and the label has one or more foils in the transition area. At least one first weakening element is provided in at least one foil in the transition area of the label. The weakening element has an orientation deviating from the first direction.

22 Claims, 6 Drawing Sheets

LABEL FOR PLACING ON A SYRINGE BODY, AND SYRINGE BODY

CROSS REFERENCE TO RELATED APPLICATIONS

Applicants claim priority under 35 U.S.C. §119 of German Application No. 10 2009 039 572.5 filed Sep. 1, 2009.

BACKGROUND OF THE INVENTION

The application relates to a label for placing on a syringe body, and to a syringe body provided with this label.

In medicine and other fields, active substances, for example medications, are administered with the aid of a syringe, the syringe having a syringe body (mostly of plastic or glass) and a stopper or plunger movable therein. At its front end, the syringe can be connected or is already connected to a syringe needle. The syringe body and syringe needle are often manufactured in one piece, for example in the form of a syringe needle let into a syringe body made of glass.

In order to reduce the risk of injury when handling the syringe and when transporting it, the syringe needle is covered by a cap, which is fitted onto the syringe needle. The cap is pressed in the axial direction against the holder of the syringe needle.

This is done mechanically during the production and packaging of the syringe. However, after the syringe has been used, there is a risk of injury when the cap is pressed back onto the needle or onto the surrounding front end of the syringe body.

In the field of medicine, for example, it is therefore customary to provide syringes additionally with a needle-receiving means, which is mounted laterally on the syringe body, next to the holder of the syringe needle. Such a needle-receiving means can be pressed laterally against the syringe needle, and the syringe needle is admitted lengthwise into a corresponding recess or depression of the needle-receiving means. After use of a syringe, in particular of a syringe for medication, the risk of injury posed by the exposed syringe needle can be reduced in this way, specifically without the original cap having to be fitted back in place for this purpose.

Needle-receiving means of the type described here are known from U.S. Pat. No. 3,658,061 and from US 2007/0260191 A1.

From WO 2006/105807, it is known that a needle-receiving means of this kind, for subsequent protection of the syringe needle, can be designed in the form of a label. The label is produced using foils, with a first foil portion being able to be wound around the syringe body. The needle-receiving means, which can be pressed on against the syringe needle, is connected pivotably to the first foil portion with the aid of a transition area. While the first foil portion of the label surrounds the syringe body and is affixed to the outer wall of the syringe body, the transition area and at least the needle-receiving means for securing the syringe needle protrude in a first axial direction beyond the shoulder of the syringe body. After the liquid in the syringe, for example the medication solution, has been administered, the needle-receiving means is pressed laterally onto the exposed syringe needle.

A problem lies in the design of the transition area between the affixed first foil portion and the needle-receiving means for the syringe needle. This transition area serves for the movable, in particular pivotable, securing of the needle-receiving means on the syringe body. Depending on the angle position of the needle-receiving means relative to the syringe needle, the needle-receiving means is more or less in the way during the administration from the syringe. It proves difficult to design the transition area in such a way that defined angle positions of the protruding needle-receiving means relative to the syringe needle are adopted automatically, without the user having to pivot the needle-receiving means back or having to correct the angle position by hand. Particularly when the needle-receiving means has already been pivoted back and forth several times during unpacking, or for some other reasons, it is not possible, in conventional designs, to ensure that the needle-receiving means always readopts the predefined angle positions, for example near the syringe needle or at a great angle away from the latter. Instead, the transition area is weakened or even damaged by being repeatedly pivoted back and forth.

It would be desirable to provide a label for placing on a syringe body, in which label the orientation or angle position of the needle-receiving means relative to the direction of the syringe needle is reliably recovered automatically, particularly even when the needle-receiving means has been pivoted back and forth several times.

SUMMARY OF THE INVENTION

According to the application, a label for placing on a syringe body is provided, which label comprises the following:
  a first foil portion, which can be wound around a syringe body,
  a needle-receiving means for a syringe needle, for protecting against injuries by the syringe needle, the needle-receiving means having at least one second foil portion and a shaped plastic part that can be pressed on laterally against the syringe needle, and
  a transition area via which the needle-receiving means is connected pivotably to the first foil portion, the transition area protruding laterally over the first foil portion in a first direction, and the label having one or more foils in the transition area,
    wherein at least one first weakening element is provided in at least one foil in the transition area of the label,
    wherein the at least one first weakening element has an orientation deviating from the first direction.

According to the invention, a defined arrangement of one or more weakening elements can be provided in the transition area of the label, wherein the arrangement comprises at least one first weakening element by which at least one foil of the label is weakened, for example locally interrupted, and wherein the first weakening element is arranged in an orientation deviating from the first direction. In the case of a label wound around a syringe body, such a weakening element according to the application permits a defined orientation and adjustment of defined angle positions that make handling of the syringe easier. According to one embodiment, two separate first weakening elements can be provided, particularly in mirror inversion to each other.

According to other embodiments, second weakening elements can additionally be provided which are likewise formed in at least one foil of the label but, in contrast to the first weakening elements, extend in the axial direction. Thus, for example, two second weakening elements can be arranged on opposite sides of the first weakening element or of a pair of first weakening elements and can be spaced apart from the first weakening element(s) and from each other. In particular, one of the two second weakening elements can be arranged in front of the first weakening element in the direction of the syringe needle, while the other second weakening element can be arranged behind the first weakening element in the direction of the syringe needle. Moreover, each second weakening element can be provided in pairs, for example each in the form of two mutually parallel second weakening elements extending alongside each other, wherein one pair of second weakening elements is arranged on one side of the at least one first weakening element (for example towards the syringe needle) and the other pair is arranged on the opposite side. The pairs of second weakening elements are separated from each other not only by the at least one first weakening element, but also by a corresponding additional axial spacing from the first weakening element. According to an alternative embodiment, one pair of second weakening elements can be provided that intersects the at least one first weakening element, i.e. crosses over or under the at least one first weakening element, depending on which foil the respective weakening element is formed in.

The combinations proposed here for the number, shape, relative position and separation of said weakening elements make it possible for a label, produced using foils, to be designed in the transition area in such a way that the angle position or angle positions to which the pivotable needle guard will tend are reliably recovered even after repeated movement back and forth, specifically without one of the foils in the transition area of the label breaking or suffering fatigue outside predetermined break points, and without the tension and spring force of the foils being lost over time. Thus, the above-described arrangement of weakening elements makes it possible, with the aid of foils, to achieve a permanent and reliable spring force in the transition area in the direction of the predefined angle positions.

The first and second areas of weakening do not have to be provided in the same foils. For example, in a label with several foils, for example two foils, the second weakening elements can be provided in a different foil from the first weakening element or additionally in another foil or only in the other foil. In this way, the spring action can be further optimized in respect of the desired angle position.

The first weakening element and/or the second weakening elements may be designed as weakening lines, i.e. as line-shaped elements, wherein the second weakening elements can extend along the first direction and the first weakening elements have another orientation and/or another profile.

The first weakening element and/or the second weakening elements are formed as cuts, perforations or other cutouts which locally interrupt or weaken at least one foil of the label in the transition area. In the area of the cut lines, the respective foil is either cut through completely or partially incised.

Alternatively, for example, the first weakening element and/or the two second weakening elements may be formed as perforations. In this case, each of these weakening elements consists of a sequence of several (at least two) partial incisions, holes, punches or other locally delimited recesses or material separations. However, the respective recesses or other cutouts of a given weakening element are arranged so close to each other that their spacing is substantially smaller than the spacing of the whole weakening element from the others. In particular, the individual incisions or material cutouts of the same weakening element are preferably arranged so tightly together that the spacing between them is no longer detectable by the naked eye and the inner structure of the weakening element thus remains concealed from view.

Between the respective weakening elements, bridge areas can be provided which, despite the weakening elements, lead to a certain degree of stabilization, which is compatible with the desired aligning behaviour in respect of the angle positions of the needle-receiving means.

The second weakening element or the second weakening elements can be arranged at the center of the width of the transition area and can extend collinearly. The width of the transition area influences the azimuthal range along the circumference of the syringe body around which the transition area of the label extends.

Provision is preferably made that the at least one first weakening element as a whole extends transversely with respect to the first direction. The first weakening line can be formed, for example, as a straight or curved cut or as a similarly line-shaped but differently structured weakening line. In the case of a curved profile, the overall direction need only lie approximately transversely with respect to the first axial direction or need only have a sufficiently large angle deviation in relation to the first direction.

For example, the at least one first weakening element can have a curved profile in which a central area reaches closer to the needle-receiving means for the syringe needle than do two outer ends of the at least one first weakening element.

The label can have a first foil and a second foil, the surface area of both foils including at least the transition area. It is thus possible to optimize the desired orientation of the needle-receiving means in respect of turning or snapping back to desired angle positions, due to both foils being provided with the weakening elements in different ways in the transition area. The foils can be plastic foils or paper foils for example.

The at least one first weakening element can be formed in the second foil, but not in the first foil. This second foil can, for example, be a lower foil, preferably also thicker and more torsionally rigid.

Moreover, the second weakening element or the second weakening elements can be formed both in the first foil and in the second foil. This increases the influence of the second weakening elements on the angle orientation behaviour.

The foil provided with the at least one first weakening element can have, between the first weakening element and each of the second weakening elements arranged along the first direction, a respective first bridge area. In this respective first bridge area, the respective foil preferably has an unreduced layer thickness or at least a greater layer thickness than along the course of the first weakening element.

Moreover, laterally outside two ends of the first weakening element, i.e. in the azimuthal direction on both sides of the first weakening element, the foil provided with the at least one first weakening element can have a respective second bridge area of unreduced layer thickness. The bridge areas contribute to the tension within the transition area of the label when an unfavourable pivot angle is adopted, and they thus cause the needle-receiving means to snap forwards or back to the angle position closer to or further away from the syringe needle.

The first foil is preferably an upper foil, and the second foil is preferably a lower foil which is arranged under the first foil and at the same time above the shaped plastic body. The second foil, which is provided for example as the only one with the first weakening element, is therefore arranged between the first foil and the shaped plastic part. The shaped plastic part is also preferably an injection-moulded part. It can in particular have barbs on the underside which, after application, faces towards the syringe needle. Upon pressing against the syringe needle, or also upon further bending of the syringe needle by still greater pressure, the syringe needle then engages in corresponding barbs; the needle-receiving means remains permanently on the needle tip and surrounds the latter so as to protect the user from injury.

The surface area of the first foil preferably extends over the first foil portion, the transition area and the needle-receiving means. In particular, the first foil portion of the label can be formed exclusively from the first, preferably upper/outer foil. The first foil portion of the label is the region with the greatest surface area, since it is wound around the circumference of the syringe body. By contrast, the transition area and/or the foil section in the area over the shaped plastic body will extend only by a smaller azimuthal circumference angle around the syringe needle.

The surface area of the second foil preferably extends over the transition area and the needle-receiving means. For example, the second foil can extend over the entire outer face of the shaped plastic body which (except for possible cutouts or depressions) is predominantly smooth. Moreover, the second and preferably lower foil can extend beyond the transition area as far as a directly adjacent, approximately semicircular, conical or in some other way tapering partial area of the first foil area.

The second foil is preferably thicker and/or more torsionally rigid than the first foil. For example, the second foil can have a layer thickness of between 50 and 200 μm, whereas the first, preferably outer foil can be provided with a layer thickness of 25 to 100 μm, for example.

With the aid of the transition area by which it is connected to the first foil area, the needle-receiving means for the syringe needle can be pivoted between a first angle position and a second angle position into which the needle-receiving means respective snaps. Between both angle positions or angle position areas there then lies an area of less stable angle positions, from which a snapping forwards or backwards into the preferred front or rear angle position takes place automatically. This facilitates the use of the syringes during and after injection.

The first angle position is preferably in the range between 0° and 20° relative to the first direction, and that the second angle position is in the range between 50° and 80° relative to the first angle position.

A syringe body provided with the label according to the application, for example with the label affixed thereto, makes the injection procedure and the handling of the syringe easier since, by virtue of the inventive design of the transition area, the needle-receiving means, which is of course needed only after the injection, automatically takes up a predefined angle position (particularly in a direction obliquely inclined with respect to the direction of the syringe needle), and does so even after being repeatedly pivoted back and forth. In this way, the needle-receiving means, protruding in a predefined angle position, does not get in the way when applying the syringe and when performing the injection, even to a considerable depth beneath the skin.

BRIEF DESCRIPTION OF THE DRAWINGS

A number of illustrative embodiments are described below with reference to the figures, in which.

DETAILED DESCRIPTION OF THE EMBODIMENTS

Figure 1:
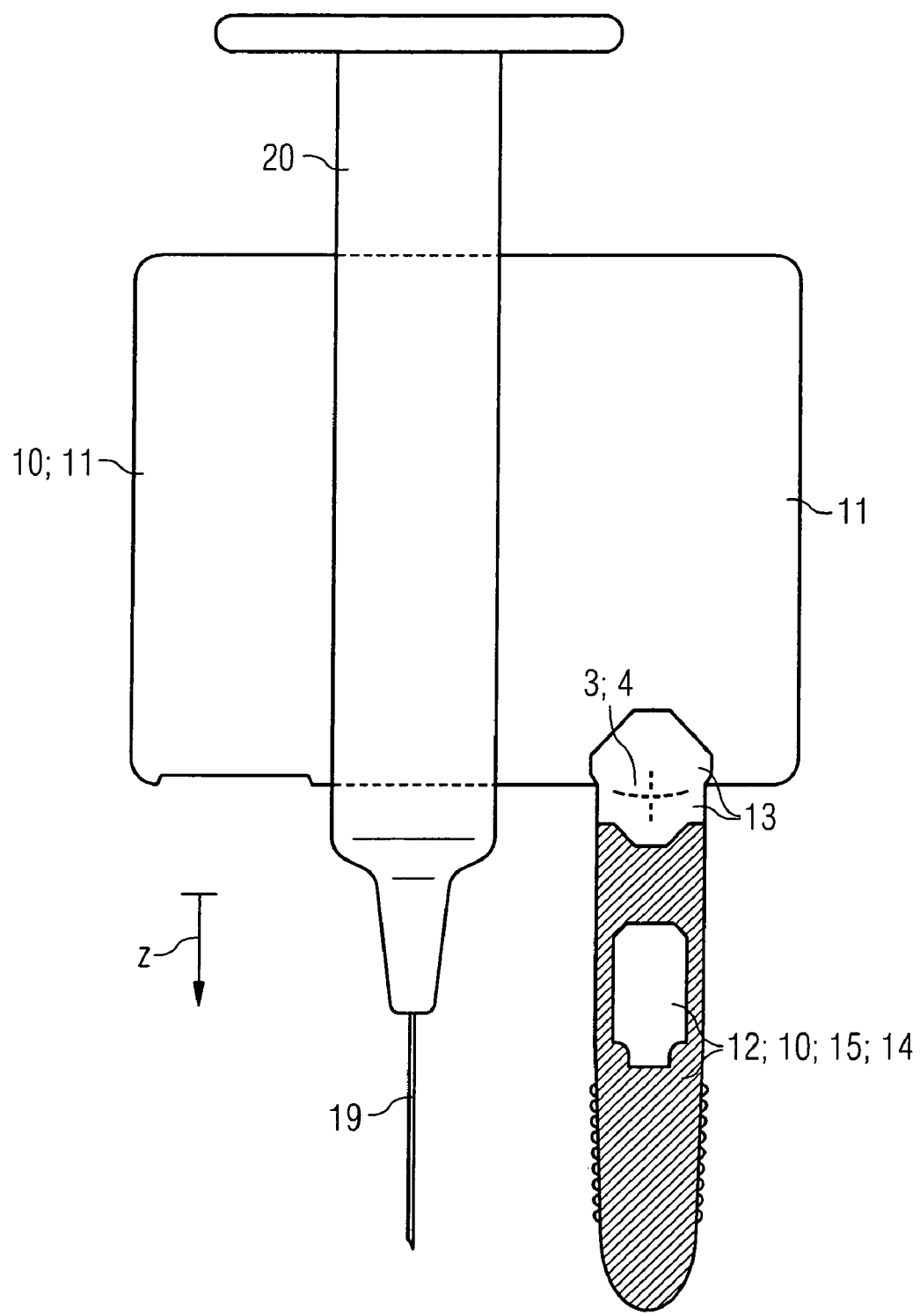
FIG. 1 shows a schematic view of an illustrative embodiment of a label according to the application and of a syringe that is to be provided with same.

FIG. 1 shows a schematic view of an embodiment of a label 10 according to the application, and of a syringe 20 on whose syringe body 20 the label 10 is applied. The first foil portion 11, which is shown in FIG. 1 as being approximately rectangular, rolls at least partially around the circumference of the syringe body 20. By contrast, a second foil portion 12 of the label 10 protrudes laterally from the first foil portion 11 in a first direction corresponding to the axial direction z of the syringe. The axial direction z is the direction in which the syringe needle 19 points, which syringe needle 19 is or can be connected to the syringe body 20.

A shaped plastic part 14 is mounted on the second foil portion 12 of the label 10 and can be pressed inwards against the syringe needle 19. In this way, the syringe needle 19 is enclosed and can thus engage in a corresponding locking means, for example in several hooks or barbs on the shaped plastic part 14. After the liquid in the syringe has been administered, there is therefore no longer any risk of injury when the syringe needle 19 is secured in this way.

Between the first foil portion 11 and the needle-receiving means 15 of the label 10, a transition area 13 of the label is provided (for flexible and therefore pivotable connection of the needle-receiving means 15 and of the attached first foil portion 11). The transition area 13 not only ensures a pivotable and at the same time secure connection of the needle-receiving means 15 to the syringe body 20, but also ensures that the orientation of the needle-receiving means 15 is automatically set in one or more predefined angle positions relative to the axial direction z, such that the receiving means 15, on the one hand, does not get in the way during the injection and, on the other hand, can nevertheless be pressed effortlessly against the syringe needle 19.

The receiving means 15 thus comprises, in addition to the shaped plastic part 14, also a second foil portion 12, which can be formed from one or more foils. The second foil portion is therefore a surface area of the overall foil making up the label, specifically the foil portion to which the shaped plastic part 14 is affixed. Also in the first foil portion 11 and/or in the transition area 13, one or more foils can be provided on one another and are connected there to form an overall foil.

A first foil is preferably provided whose surface area extends over the first foil portion 11, the transition area 13 and the needle-receiving means 15. Moreover, a second foil is preferably provided which, however, preferably only extends over the transition area 13 and the needle-receiving means 15.

The first foil portion 11 is therefore preferably formed from only a single foil layer. The other surface areas are preferably of multi-layer design (namely of at least the first foil and the second foil), particularly in order to achieve the automatic adoption of defined angle positions in which the needle-receiving means 15 is intended to point during and/or after the injection.

Figure 2:
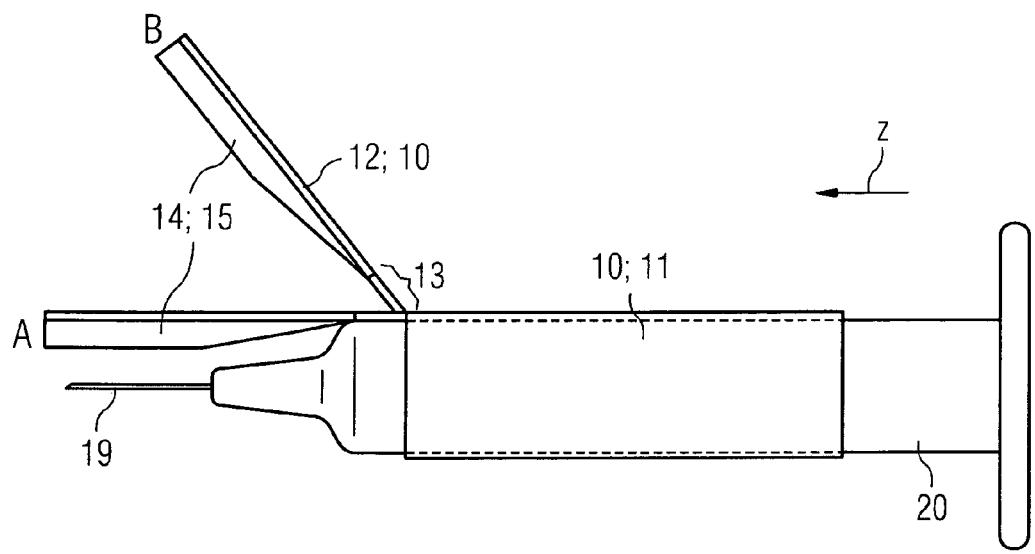
FIG. 2 shows a cross-sectional view in relation to FIG. 1, with attached label and with two different angle positions of a needle-receiving means of the label.

FIG. 2 shows a schematic cross-sectional view in relation to FIG. 1. The label 10, still loose in FIG. 1, has now been wound with its first foil portion 11 around the syringe body 20. The needle-receiving means 15, with its shaped plastic part 14 and with the second foil portion 12, is shown twice in FIG. 2, namely in two different angle positions A and B. Whereas this needle guard is pressed downwards after the injection, i.e. against the syringe needle 19, it can be opened out beforehand by a maximum of 180°. In the delivery state, this needle-receiving means 15 will point in the direction z, which corresponds to the first angle position A of preferably 0° or at least of between 0° and 20° relative to the direction z.

Moreover, when suitably deflected for the first time by hand, the needle-receiving means 15 should as far as possible automatically adopt a second angle position B, which preferably lies in the range of between 50° and 80° relative to the direction z. Between these two angle positions A, B, there should be an unstable area of angle positions in which the needle guard snaps back automatically either in the direction of angle position A or in the direction of angle position B. Angle position B allows injection to be easily carried out, whereas angle position A is advantageous after the injection for pressing against the syringe needle 19. The purpose of the transition area 13, which consists of two foil layers for example, is to ensure the spontaneous adoption of the respective angle position A or B. For example, in the event of a considerable excursion of greater than 90° relative to the direction z, the needle-receiving means 15 should snap forwards in the direction of angle position B and should remain there as long as it is not moved manually by the user.

Figure 3A:
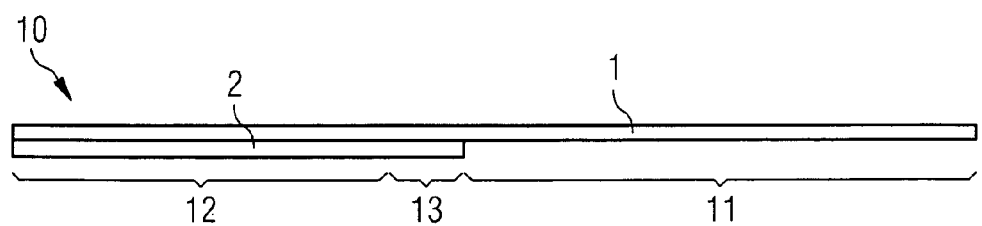
FIG. 3A shows a cross-sectional view of an illustrative embodiment of a label along the line of symmetry of the needle-receiving means.

FIG. 3A shows a cross-sectional view of an illustrative embodiment of a label along the line of symmetry of the needle-receiving means, for example for the label from FIGS. 1 and 2. The figure illustrates the layer structure of the label, which is shown without the shaped plastic part 14. As can be seen from FIG. 3A, the label has a first foil 1 and a second foil 2, wherein the surface area of the first foil 1 includes the first foil portion 11, the transition area 13 and the second foil portion 12 to be affixed to the shaped plastic part 14. By contrast, the surface area of the second foil 2 comprises only the transition area 13 and the second foil portion 12. The label foil thus preferably consists of two foils 1, 2. The second, lower foil 2 is preferably thicker and/or more torsionally rigid than the upper, first foil 1.

Figure 3B:
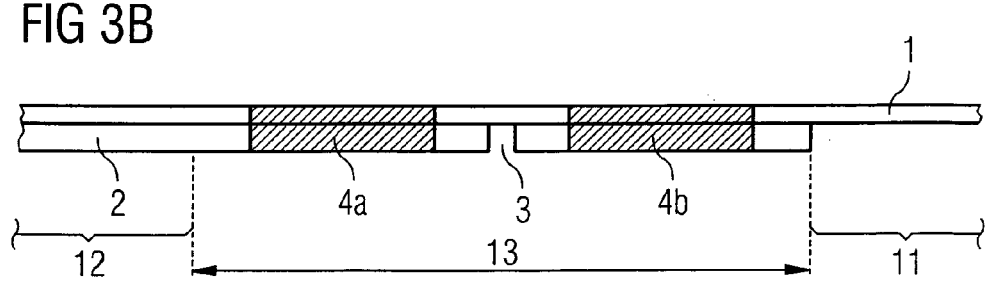
FIG. 3B shows an enlarged detail from FIG. 3A.

FIG. 3B shows an enlarged detail from FIG. 3A and also indicates the arrangement of the weakening elements 3, 4a, 4b. The sectional plane shown in FIG. 3B extends, as in FIG. 3A, through the centre of the needle-receiving means 15 (see the plan view in FIG. 1). Thus, in FIG. 3B, the weakening lines or cut lines that correspond to the weakening elements 4a, 4b extend in the plane of the drawing; they are indicated by the hatched areas. As can be seen from FIG. 3B, the weakening elements 4a, 4b in this illustrative embodiment are formed in the upper foil 1 and also in the lower foil 2. By contrast, the first weakening element 3 is formed only in the lower foil which, in accordance with the section extending transversely with respect to the plane of the drawing, is interrupted or cut through in the centre of the transition area. The precise arrangement of the weakening lines or cut lines can also be chosen, for example, according to one of the illustrative embodiments explained in more detail below. Likewise, these and the subsequent illustrative embodiments can be varied as regards the respective foil or foils in which the individual weakening elements are to be formed.

Figure 4:
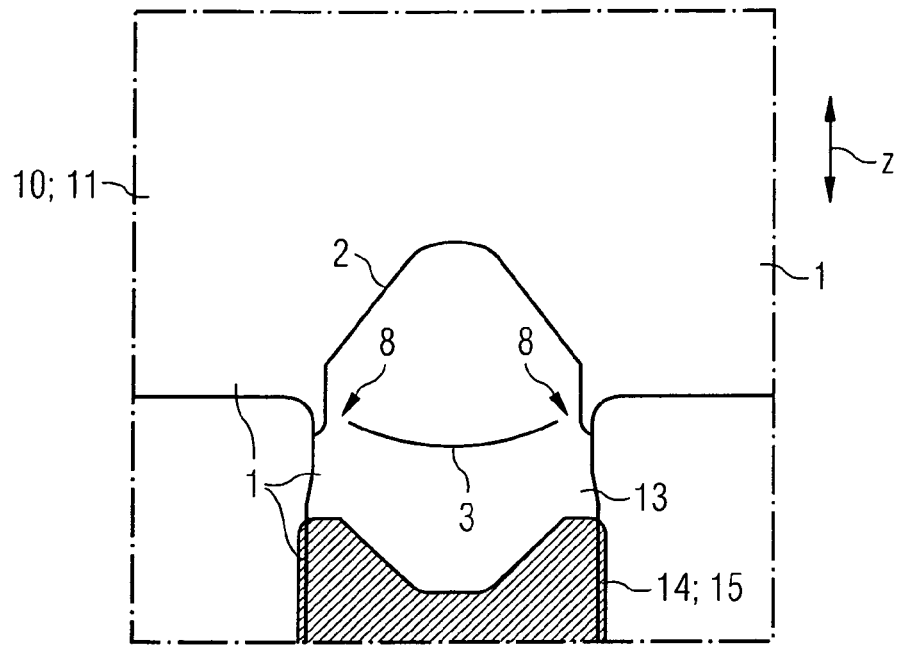
FIG. 4 shows an enlarged detail of the label from FIG. 1 according to a first illustrative embodiment.

FIG. 4 shows an enlarged detail of the label from FIG. 1 according to a first illustrative embodiment. The figure illustrates the transition area 13 which connects the first foil portion 11 of the label 10 to the needle-receiving means 15 of the label. The shaped plastic part 14 is shown by hatching in FIG. 4; the shaped part is mounted on the underside of the second foil portion 12 directed towards the syringe needle.

The transition area 13 of the label is formed basically from one or more foils, for example plastic foils and/or paper foils. The foils of the transition area 13 can merge directly into the foils of the first and/or second foil portion and can thus merely be surface areas of larger foils extending beyond the transition area.

The transition area 13 is regarded here as that area which, on the one hand, no longer lies fixedly on the syringe body or is no longer adhesively connected to the latter and which, on the other hand, does not reach as far as the solid shaped plastic part (for example an injection moulded part). The transition area 13 is therefore a flexible foil surface section not yet fixed to rigid shaped parts by adhesive coatings on its underside. The transition area 13, as hinge connection or pivot connection, permits the lateral excursion, i.e. orientation, of the (tangentially forwardly protruding) needle-receiving means 15 relative to the first direction. Thus, the needle-receiving means 15 can be pivoted upwards or downwards by suitable bending of the label foil or label foils in the transition area 13. Particularly in the transition area, the label foil can consist of several layers, i.e. partial foils.

The label foil of the label 10 preferably comprises a first foil 1 and a second foil 2 (for example of plastic or paper), wherein the surface area of the first foil 1 preferably extends at least over the first foil portion 11 and over the transition area 13, preferably also over the lateral extent of the needle-receiving means 15. The surface area of the second foil 2 preferably comprises the transition area 13 and the lateral dimensions of the needle-receiving means 15. Particularly in the transition area 13, two foils are preferably provided one on top of the other.

In the illustrative embodiments according to FIGS. 4 to 11, incisions (in at least one of the foils) are also shown in the transition area 13. These incisions, which locally interrupt the foils or at least weaken them (by local reduction of the layer thickness) are later used, when the label according to the application is affixed around the cylindrical syringe body, to obtain a specific adjustment of the angle position of the protruding needle-receiving means 15. In the label according to the application, the specific arrangement, on the one hand, of weakening elements and, on the other hand, of connecting webs or bridge areas at defined positions within the transition area 13 ensures a defined adjustment behaviour of the needle-receiving means 15 in terms of the angle by which it opens further out, depending on the initial angle position, or snaps back into one of several defined angle positions. However, this behaviour is not directly obtainable from the inventive arrangement, dimensioning, size and shape of the weakening elements according to the application, and instead the resulting pivoting behaviour of the needle-receiving means 15 is seen only after the label according to the application has been applied to the cylindrical, conical or otherwise curved outer jacket of the syringe body.

According to the first embodiment in FIG. 4, a first line-shaped weakening element 3 is provided, specifically a curved weakening line that extends almost as far as both lateral ends of the transition area 13.

In FIG. 4, the first foil 1 is preferably an upper foil, and the second foil 2 is a second foil arranged between the first foil 1 and the shaped plastic part 14 and preferably having a greater thickness than the first foil. Preferably, only the upper, first foil is locally separated by the curved weakening element. It has been found that a configuration of the weakening elements shown in FIG. 4 (and developed on the basis of the subsequent figures) is suitable, for example, for achieving the adjustment behaviour of the needle-receiving means 15 as explained with reference to FIG. 2.

It has been found that the arrangement and configuration described here according to FIG. 4 and according to the developments described below are particularly suitable for achieving the pivoting behaviour of the needle-receiving means 15 as explained with reference to FIG. 2.

Figure 5:
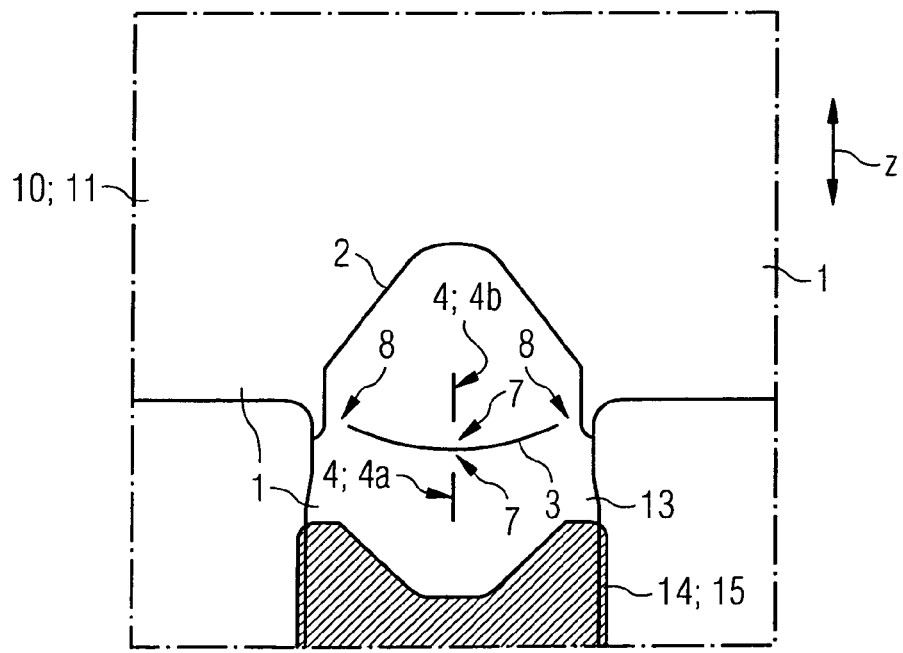
FIG. 5 shows an enlarged detail of the label from FIG. 1 according to a second illustrative embodiment.

FIG. 5 shows a second illustrative embodiment in which two axially extending second weakening elements are additionally provided, which are each spaced apart from the first weakening element 3 and point in the direction of the needle-receiving means 15, i.e. the first direction z. They are, however, arranged on opposite sides of the curved weakening element 3. These three weakening elements are preferably cuts made through one or more foils of the label in the transition area 13. For example, the shorter, axially extending weakening elements 3 are formed in both foils 1, 2.

The two weakening elements extending in the axial direction z are designated as second weakening elements 4 or 4a and 4b. As can be seen from FIG. 5, both second weakening elements 4a, 4b are spaced apart from the first weakening element 3. Between these, therefore, there is a respective first bridge area 7 to both sides of the centre of the first weakening element 3. The first bridge areas 7 serve as holding webs in order to bring back together the right-hand and left-hand foil sections next to the respective weakening element 4a, 4b, at least in the area directly at the centre of the first weakening element 3. Moreover, the first weakening element 3 does not extend entirely to the lateral edges of the transition area 13, and instead there are second bridge areas 8 there (as also in FIG. 4) in the foil in which the first weakening element 3 is formed. It will also be seen that the first weakening element 3 extends without interruption through the centre of the transition area 13, whereas the two second weakening elements 4a, 4b end at a distance outside the first weakening element 3.

Figure 6:
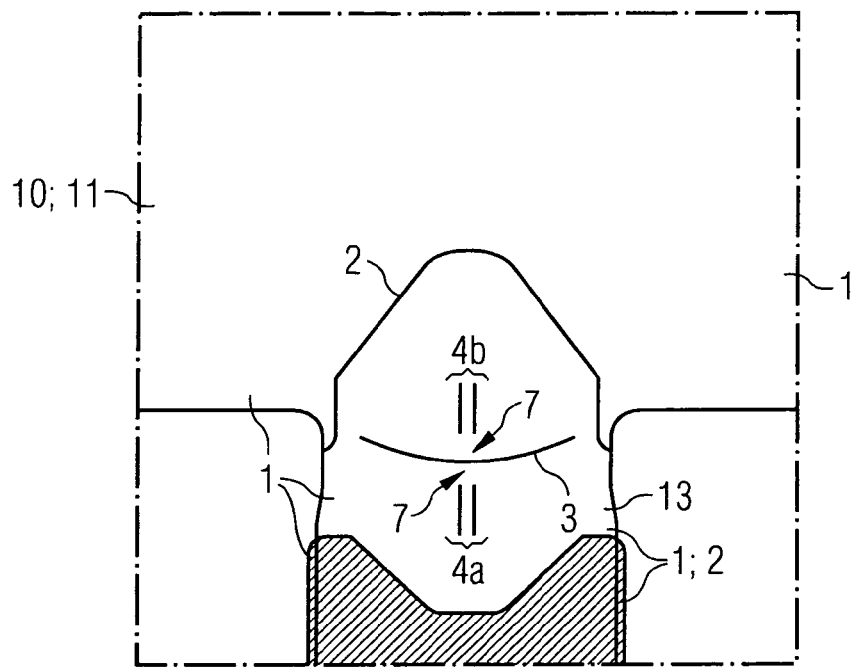
FIG. 6 shows an enlarged detail of the label from FIG. 1 according to a third illustrative embodiment.

FIG. 6 shows a third illustrative embodiment in which, instead of each second weakening element 4a, 4b from FIG. 5, a pair of respective weakening elements 4a, 4b is provided. The transition area thus has four second weakening elements which each extend parallel to each other in pairs and are spaced apart from the first weakening element 3.

Figure 7:
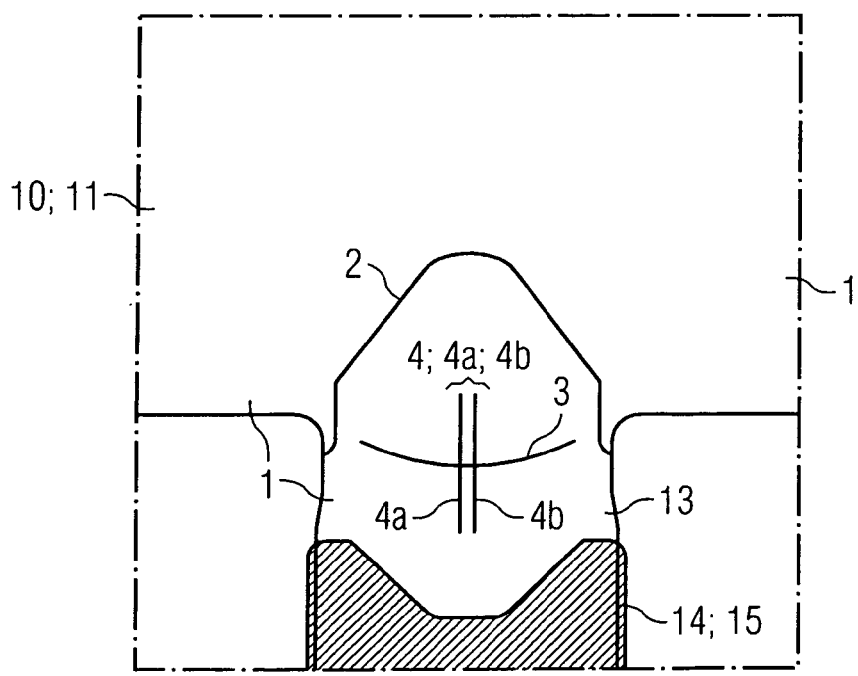
FIG. 7 shows an enlarged detail of the label from FIG. 1 according to a fourth illustrative embodiment.

FIG. 7 shows a fourth illustrative embodiment in which a pair of second weakening elements 4a, 4b is likewise provided. Compared to FIG. 6, however, the pair of second weakening elements 4a, 4b crosses the first weakening element 3, for example as a cross-over in different foils and/or as a cut through the same foil. Moreover, each of the second weakening elements 4a, 4b is so long that it extends between the outer ends of the respective second weakening elements 4a, 4b from FIG. 6. Also in FIG. 7, the two second weakening elements 4a, 4b extend in a pair parallel to each other.

Figure 8:
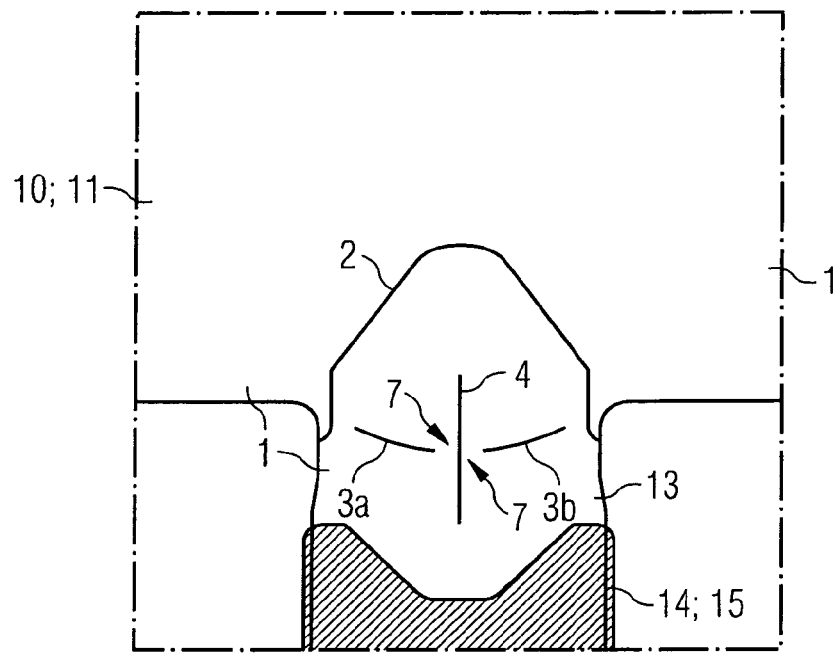
FIG. 8 shows an enlarged detail of the label from FIG. 1 according to a fifth illustrative embodiment.

FIG. 8 shows a fifth illustrative embodiment in which, instead of a single first weakening element 3 extending almost as far as both azimuthal edges of the transition area 13, two separate first weakening elements 3a, 3b (or alternatively a still greater number of first weakening elements) are provided. These extend, for example, transversely or approximately transversely with respect to the first direction z (or alternatively at an inclination, for example diagonally thereto) and are spaced apart from each other. In addition, at least one second weakening element 4 can optionally be provided extending along the first direction z. It can be arranged in the azimuthal direction between both first weakening elements 3a, 3b. Its axial position and length can be chosen such that it extends in the axial direction z partially on both sides of the pair of first weakening elements 3a, 3b and thus also through the centre between both first weakening elements 3a, 3b.

Figure 9:
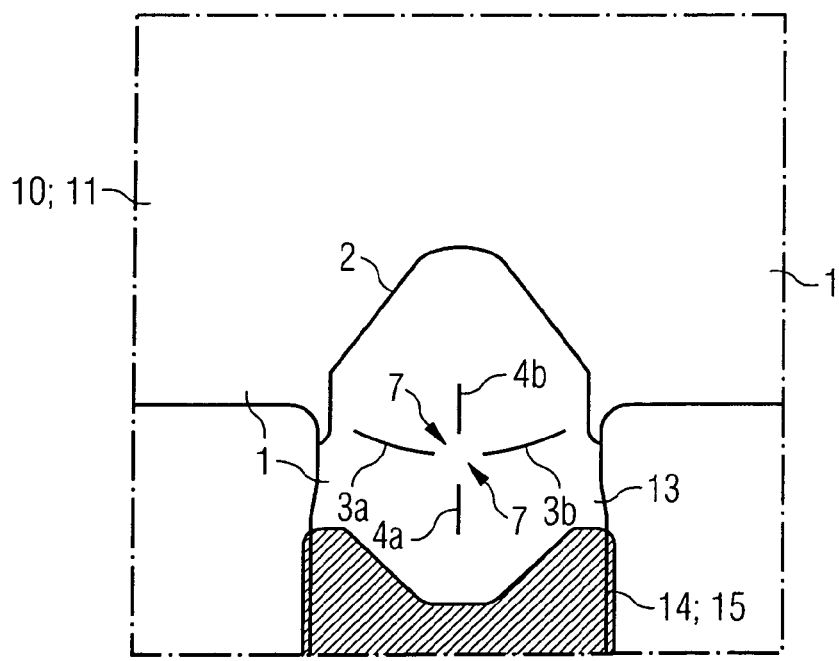
FIG. 9 shows an enlarged detail of the label from FIG. 1 according to a sixth illustrative embodiment.

FIG. 9 shows a sixth illustrative embodiment in which, compared to FIG. 8, and instead of the single axially extending second weakening element 4, two separate second weakening elements 4a, 4b are provided. These extend along the first direction z, one on each side of the pair of first weakening elements 3a, 3b, and are spaced apart from these and also from each other. The transition area thus has four weakening elements 3a, 3b, 4a, 4b which each extend in succession in pairs and are spaced apart from all the other weakening elements.

In FIG. 9, therefore, between the weakening elements 3a, 3b, 4a, 4b, there is only a single, but particularly stable first bridge area 7, whereas two separate first bridge areas 7 are provided in each of FIGS. 5, 6 and 8.

Figure 10:
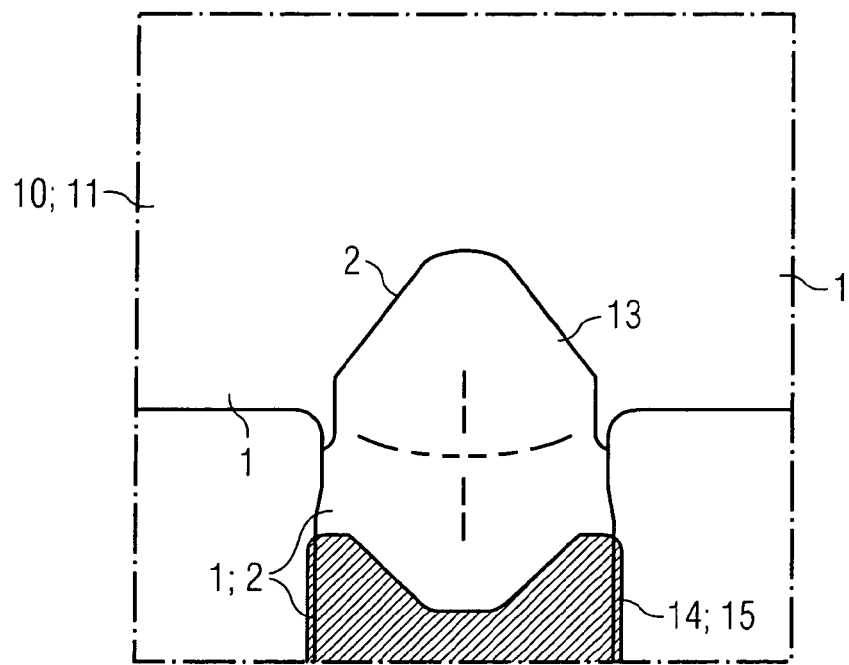
FIG. 10 shows an alternative embodiment with a microstructure of the weakening elements, explained on the basis of the illustrative embodiment from FIG. 5.

FIG. 10 shows, on the basis of the illustrative embodiment from FIG. 5, an alternative embodiment in which the weakening elements are formed by perforations. The other illustrative embodiments in FIGS. 4 and 6 to 9 can also be modified in the manner described below. According to FIG. 10, the weakening elements are not therefore continuous cuts, and instead they consist of a juxtaposition of punched holes, gaps, partial cuts or other cutouts or folds along the line profile of the respective weakening line or of the respective weakening element 3, 4a, 4b.

Figure 11:
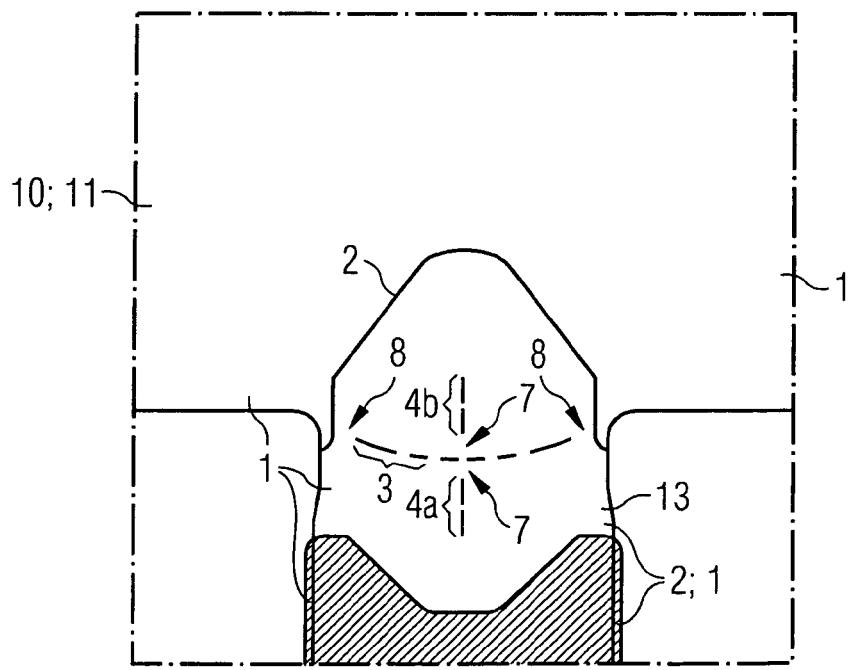
FIG. 11 shows the embodiment from FIG. 10 with additional identification of the respective weakening elements structured by the microstructure.

FIG. 11 shows the same embodiment as FIG. 10, but with additional reference signs for identifying the respective weakening elements and bridge areas. As can be seen from FIG. 11, each of the weakening elements 3, 4a, 4b is further divided, i.e. formed not as a continuous weakening line or cut line, but instead as a perforation or otherwise interrupted weakening line or cut line. The two second weakening elements 4a, 4b can, for example, be divided into two or more closely adjoining partial lines. The distance between these partial lines within the respective second weakening element 4 is smaller than the distance of this weakening element from the first weakening element 3, i.e. smaller than the width of the first bridge area 7 in the axial direction.

It will also be seen in FIG. 11 that the first weakening element 3 is also formed as a perforation made up of (for example six) partial lines. Here too, the distance between the partial lines is much smaller than the width of the second bridge areas 8 in the direction transverse to the axial main direction of the needle-receiving means 15 and in particular also smaller than the axial extent of the first bridge areas 7. This results in a microstructure of the weakening elements, although the weakening elements, when seen from outside, initially appear only as homogeneous, uninterrupted lines. The interruptions between the individual lines of the first weakening element are in particular predetermined break points or predetermined tear points at which the foil provided with them tears (not perceptibly to the user) as soon as the needle-receiving means of the label applied to the syringe body is opened out for the first time. All or only some of the weakening elements provided in the illustrative embodiments of FIGS. 4 to 9 can be designed according to the microstructure from FIGS. 10 and 11.

Depending on the initial angle position to which the needle-receiving means 15 is brought manually by the user, it snaps back to one or more angle positions or angle position areas, for example to angle position A or B from FIG. 2. Even when the needle guard is moved back and forth repeatedly, the hinge connection according to the application in the transition area 13 guarantees a reliable pivoting behaviour, even upon repeated stressing and angle adjustment by the user. The stability, resistance and durability of the hinge connection designed according to the application are therefore greater than in conventional syringe labels.

What is claimed is:

1. A label for placing on a syringe body, comprising:
    a first foil portion adapted to be wound around a syringe body;
    a needle-receiving means for a syringe needle for protecting against injuries by the syringe needle, said needle-receiving means having at least one second foil portion and a shaped plastic part adapted to be pressed on laterally against the syringe needle; and
    a transition area via which the needle-receiving means is connected pivotably to the first foil portion, the transition area protruding laterally over the first foil portion in a first direction, and the label having one or more foils in the transition area,
    wherein the transition area of the label comprises at least one weakening element in at least one foil, and
    wherein the at least one weakening element comprises at least one first weakening element and at least one second weakening element, wherein the at least one second weakening element extends along a first direction and the at least one first weakening element has an orientation deviating from the first direction;
    wherein the at least one weakening element permits a defined orientation and adjustment of the needle-receiving means in one or more defined angle positions relative to the first direction;
    wherein at least one of the first and second weakening elements are designed as cut lines, perforations or other cutouts, which locally interrupt or weaken the at least one foil of the label in the transition area; and
    wherein laterally outside two outer ends of the at least one first weakening element, the foil provided with the at least one first weakening element has a respective second bridge area of unreduced layer thickness.

2. The label according to claim 1, wherein the transition area of the label has, in at least one foil, at least two of said first weakening elements that have an orientation deviating from the first direction.

3. The label according to claim 2, wherein the two first weakening elements, in an azimuthal direction, are arranged with mirror inversion to each other on opposite sides from a center of the transition area of the label.

4. The label according to claim 1, wherein said at least one first weakening element extends transversely with respect to the first direction.

5. The label according to claim 1, wherein the at least one first weakening element has a curved profile, and a part of the at least one first weakening element arranged in the center of the transition area reaches closer to the needle-receiving means than do two outer ends of the at least one first weakening element.

6. The label according to claim 1, wherein the transition area of the label has at least two of said second weakening elements in at least one foil.

7. The label according to claim 6, wherein the second weakening elements are arranged on opposite sides of the at least one first weakening element and are each spaced apart from the at least one first weakening element.

8. The label according to claim 6, wherein the second weakening elements are arranged next to each other and each cross or intersect the at least one first weakening element.

9. The label according to claim 6, wherein two respective second weakening elements are arranged on opposite sides of the at least one first weakening element and are each spaced apart from the at least one first weakening element.

10. The label according to claim 1, wherein the at least one second weakening element extends along the first direction.

11. The label according to claim 1, wherein the at least one second weakening element, in an azimuthal direction, is arranged in a center between two outer ends of the at least one first weakening element.

12. The label according to one of claim 1, wherein the label has a first foil and a second foil, a surface area of both foils includes at least the transition area.

13. The label according to claim 12, wherein the at least one first weakening element is formed in the second foil, but not in the first foil.

14. The label according to claim 12, wherein the at least one second weakening element is formed both in the first foil and in the second foil.

15. The label according to claim 12, wherein the first foil is an upper foil, and the second foil is a lower foil which is arranged between the first foil and a shaped plastic part.

16. The label according to claim 12, wherein a surface area of the first foil extends over the first foil portion, the transition area and the needle-receiving means, and wherein a surface area of the second foil extends over the transition area and the needle-receiving means.

17. The label according to claim 12, wherein the second foil is thicker or more torsionally rigid than the first foil.

18. The label according to claim 1, wherein, in the transition area, the at least one foil has at least one first bridge area of unreduced layer thickness between the at least one first weakening element and the at least one second weakening element.

19. The label according to claim 1, wherein the needle-receiving means is pivotable between a first angle position and a second angle position in which the needle-receiving means remains, with the aid of the transition area by which the needle receiving means is connected to the first foil portion.

20. The label according to claim 19, wherein the first angle position is in a range of between 0° and 20° relative to the first direction, and wherein the second angle position is in a range of between 50° and 80° relative to the first direction.

21. The label according to claim 1, wherein the at least one foil comprises at least one plastic foil or at least one paper foil.

22. A syringe body with a syringe needle and a label according to claim 1, wherein the first foil portion of the label is affixed along a circumference of the syringe body.

* * * * *